US009726871B2

(12) United States Patent
Pristinski et al.

(10) Patent No.: US 9,726,871 B2
(45) Date of Patent: Aug. 8, 2017

(54) DETECTION SYSTEM WITH ONE-PIECE OPTICAL ELEMENT TO CONCENTRATE AND HOMOGENIZE LIGHT

(71) Applicant: Bio-Rad Laboratories, Inc., Hercules, CA (US)

(72) Inventors: Denis Pristinski, Dublin, CA (US); David P. Stumbo, Pleasanton, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 667 days.

(21) Appl. No.: 14/170,394

(22) Filed: Jan. 31, 2014

(65) Prior Publication Data

US 2014/0218719 A1 Aug. 7, 2014

Related U.S. Application Data

(60) Provisional application No. 61/759,928, filed on Feb. 1, 2013.

(51) Int. Cl.

| G01N 15/14 | (2006.01) |
|---|---|
| G02B 19/00 | (2006.01) |
| G01N 35/08 | (2006.01) |
| G01N 21/64 | (2006.01) |
| F21V 8/00 | (2006.01) |
| G01N 15/10 | (2006.01) |
| G02B 6/26 | (2006.01) |

(52) U.S. Cl.
CPC ..... *G02B 19/0028* (2013.01); *G01N 15/1434* (2013.01); *G01N 15/1459* (2013.01); *G01N 21/645* (2013.01); *G01N 35/08* (2013.01); *G02B 6/0008* (2013.01); *G01N 2015/1006* (2013.01); *G01N 2021/6478* (2013.01); *G01N 2201/0806* (2013.01); *G02B 6/262* (2013.01); *G02B 19/0076* (2013.01)

(58) Field of Classification Search
CPC .................................................. G02B 19/0028
See application file for complete search history.

(56) References Cited

U.S. PATENT DOCUMENTS

| 5,357,101 A | 10/1994 | Plesko |
|---|---|---|
| 5,731,875 A * | 3/1998 | Chandler ............. G02B 6/4249 356/336 |
| 5,739,902 A | 4/1998 | Gjelsnes et al. |
| 6,483,096 B1 | 11/2002 | Kunz et al. |

(Continued)

FOREIGN PATENT DOCUMENTS

DE 102010014359 A1 10/2011

OTHER PUBLICATIONS

Shane Thomas, Authorized Officer, International Searching Authority, U.S. Patent and Trademark Office, "International Search Report" in connection with related PCT Patent Application No. PCT/US2014/014294, dated May 16, 2014, 3 pages.

(Continued)

*Primary Examiner* — Rebecca C Bryant
(74) *Attorney, Agent, or Firm* — Kolisch Hartwell, P.C.

(57) ABSTRACT

Detection system comprising an examination region, a one-piece optical element including a focusing portion to concentrate light received from the examination region and a guiding portion to homogenize light received from the focusing portion, and a detector configured to detect homogenized light received from the guiding portion.

10 Claims, 6 Drawing Sheets

(56) References Cited

U.S. PATENT DOCUMENTS

| | | | |
|---|---|---|---|
| 2005/0175363 A1 | 8/2005 | Kim et al. | |
| 2010/0320363 A1 | 12/2010 | Schleipen | |
| 2012/0006382 A1* | 1/2012 | Dagli | G02B 17/002 |
| | | | 136/246 |
| 2012/0258549 A1 | 10/2012 | Lu et al. | |
| 2014/0160784 A1* | 6/2014 | Badahdah | H01L 31/0543 |
| | | | 362/558 |

OTHER PUBLICATIONS

Shane Thomas, Authorized Officer, International Searching Authority, U.S. Patent and Trademark Office, "Written Opinion of the International Searching Authority" in connection with related PCT Patent Application No. PCT/US2014/014294, dated May 16, 2014, 6 pages.

European Patent Office, "Extended European Search Report" in connection with related European Patent Application No. 14746906.8, dated Nov. 17, 2016, 11 pages.

European Patent Office, "Partial Supplementary European Search Report" in connection with related European Patent Application No. 14746906.8, dated Aug. 2, 2016, 6 pages.

\* cited by examiner

DETECTION SYSTEM WITH ONE-PIECE OPTICAL ELEMENT TO CONCENTRATE AND HOMOGENIZE LIGHT

CROSS-REFERENCE TO PRIORITY APPLICATION

This application is based upon and claims the benefit under 35 U.S.C. §119(e) of U.S. Provisional Patent Application Ser. No. 61/759,928, filed Feb. 1, 2013, which is incorporated herein by reference in its entirety for all purposes.

CROSS-REFERENCES TO OTHER MATERIALS

This application incorporates by reference in their entireties for all purposes the following patent documents: U.S. Pat. No. 7,041,481, issued May 9, 2006; U.S. Patent Application Publication No. 2010/0173394 A1, published Jul. 8, 2010; U.S. Patent Application Publication No. 2011/0217712 A1, published Sep. 8, 2011; U.S. Patent Application Publication No. 2012/0152369 A1, published Jun. 21, 2012; U.S. Patent Application Publication No. 2012/0190032 A1, published Jul. 26, 2012; and U.S. Patent Application Publication No. 2012/0194805 A1, published Aug. 2, 2012.

INTRODUCTION

Many biomedical applications rely on high-throughput assays of samples. For example, in research and clinical applications, high-throughput genetic tests using target-specific reagents can provide high-quality information about samples for drug discovery, biomarker discovery, and clinical diagnostics, among others. As another example, infectious disease detection often requires screening a sample for multiple genetic targets to generate high-confidence results.

Emulsions hold substantial promise for revolutionizing high-throughput assays. Emulsification techniques can create billions of aqueous droplets that function as independent reaction chambers for biochemical reactions. For example, an aqueous sample (e.g., 200 microliters) can be partitioned into droplets (e.g., four million droplets of 50 picoliters each) to allow individual sub-components (e.g., cells, nucleic acids, proteins) to be manipulated, processed, and studied discretely in a massively high-throughput manner.

Aqueous droplets can be suspended in oil to create a water-in-oil emulsion (W/O). The emulsion can be stabilized with a surfactant to reduce coalescence of droplets during heating, cooling, and transport, thereby enabling thermal cycling to be performed. Accordingly, emulsions have been used to perform single-copy amplification of nuclei acid target molecules in droplets using the polymerase chain reaction (PCR). The fraction of the droplets that are negative (or positive) for a target can be analyzed with Poisson statistics to estimate the concentration of the target in a sample.

Droplet-based assays often use one or more fluorophores as labels in droplets to report the occurrence of a reaction, such as amplification, and thus the presence or absence of at least one copy of a target in individual droplets. The droplets may be generated and reacted (e.g., thermally cycled), and then light emission is measured from each droplet to determine whether or not a target is present in the droplet. However, there are many technical hurdles to producing a light detection system for droplets that is sensitive, reliable, robust, and affordable. Some of these hurdles relate to the detection optics. For example, recently developed silicon photomultipliers combine the light sensitivity of avalanche photodiodes with a sensing area size approaching that of photomultiplier tubes, while being very compact solid state devices and manufactured at a relatively low cost. However, to make the best use of these detectors and to achieve the highest possible detector dynamic range, especially with high-speed fluorescence detection applications, it becomes important to expose the silicone photomultiplier sensing area to collected fluorescence signal evenly across all sensing elements. For weak fluorescence signals, it is equally important to avoid light losses and to provide optimal detector sensitivity.

Improved light detection systems for droplets are needed.

SUMMARY

The present disclosure provides a detection system comprising an examination region, a one-piece optical element including a focusing portion to concentrate light received from the examination region and a guiding portion to homogenize concentrated light received from the focusing portion, and a detector configured to detect homogenized light received from the guiding portion.

DETAILED DESCRIPTION

The present disclosure provides a detection system comprising an examination region, a one-piece optical element including a focusing portion to concentrate light received from the examination region and a guiding portion to homogenize light received from the focusing portion, and a detector configured to detect homogenized light received from the guiding portion.

The optical element, interchangeably termed a concentrator, may collect incident light from a relatively large area and direct it towards a light sensor with a comparatively small active area. The optical element may comprise a refractive focusing portion and a light guiding portion in one integral unit. The optical element may be a non-imaging optical device that delivers light from a relatively large input aperture (e.g., a round input aperture) to a relatively small output aperture (e.g., a rectangular output aperture), while homogenizing the intensity distribution of the light across the output aperture.

An exemplary detection system is provided. The detection system may comprise an examination region and a one-piece optical element including a head to concentrate light received from the examination region and a stem to homogenize concentrated light received from the head. The detection system also may comprise a multi-pixel detector configured to detect homogenized light received from the stem.

A method of sample examination is provided. In the method, a sample may be disposed in an examination region. Light received from the examination region may be concentrated with a one-piece optical element. The concentrated light may be homogenized with the optical element. Homogenized light received from the optical element may be detected with a multi-pixel detector.

Light intensity homogenization may be advantageous when using the optical element with multiple-pixel detectors so that no individual detector pixel gets saturated while adjacent pixels are far from saturation. An example of such a multiple-pixel detector is a silicon photomultiplier, which typically consists of tens or hundreds (or more) of individual sensing pixels. Combining the focusing portion and the light guiding portion of the optical element in a single piece ensures that the entrance to the light guiding portion is at the focal point of the focusing portion. The single piece simplifies assembly of a detection system and enables larger positional tolerances when operatively mounting the optical element with respect to a detector.

The optical element may facilitate the usage of silicon photomultipliers that have been developed over the last few years and are offered as a photomultiplier tube (PMT) replacement. The silicon photomultipliers may differ from their PMT predecessors in two important aspects: the photomultipliers may have a much smaller sensor area and may comprise a plurality of individual sensing pixels, which may be tightly-spaced. In order to serve as a direct replacement and achieve the sensitivity and dynamic range afforded by PMTs, silicon photomultipliers may be coupled with an optical device that concentrates and homogenizes light. The optical element disclosed herein is an integral device that serves both to concentrate light and to create uniform illumination of the silicon photomultiplier sensing area. A single-piece design makes manufacturing simple and ensures permanent alignment of the focusing portion with the light guiding portion.

The refractive focusing portion may have an at least substantially spherical surface with its curvature chosen to focus the incident light into a spot at the center of the entrance of the light guiding portion. The at least substantially spherical surface may be spherical (perfectly or nearly perfectly spherical) or aspherical. An aspherical surface varies slightly from a spherical shape, which may, for example, correct for spherical aberration. The at least substantially spherical surface may have an anti-reflective coating to minimize light reflection losses.

The light guiding portion may have any suitable properties. The light guiding portion may have optically smooth walls to constrain light propagating along the guiding portion due to total internal reflection. The size and shape of the light guiding portion at its light exit may be chosen to match the size and shape of a light detector for which the optical element is designed, to maximize detection of light received from the optical element. The size and shape of the light guiding portion at its light entrance may be chosen to ensure that the focused light from the focusing portion fits into the light guiding portion, for a pre-defined incident light acceptance angle for the input aperture of the optical element (and guiding portion). The respective sizes and/or the respective shapes of the light exit and light entrance of the guiding portion could be chosen to match each other for the sake of simplicity of device manufacturing. The light guiding portion could be straight or it could be bent to comply with the layout of a light-sensing device.

The detection system disclosed herein may have numerous advantages over other approaches to optical detection. These advantages may include any combination of the following: lower cost, better optical yield, and improved use of a multi-pixel detector for a single-point measurement, among others.

Further aspects of the present disclosure are presented in the following sections: (I) overview of exemplary detection systems with a light concentrator, (II) detection system with light concentrators and multi-pixel detectors, and (III) selected embodiments.

I. Overview of Exemplary Detection Systems With A Light Concentrator

Figure 1:
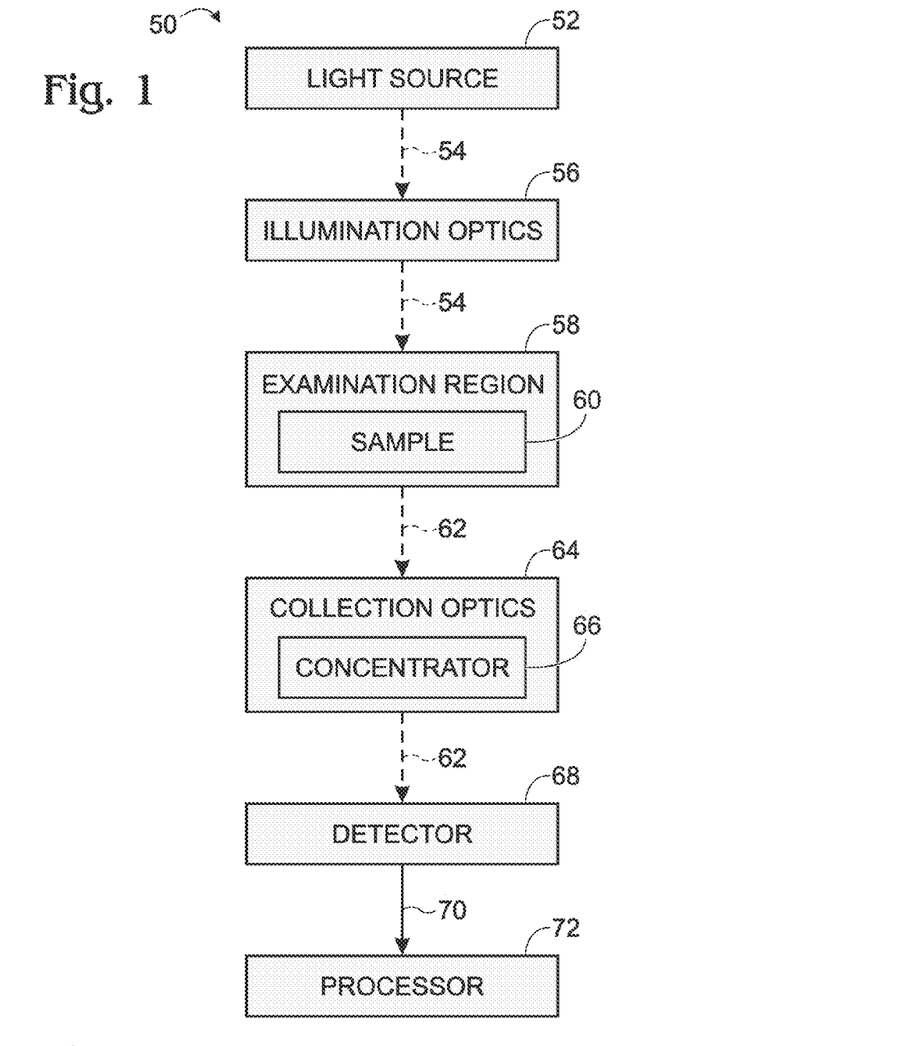
FIG. 1 is a schematic representation of selected aspects of an exemplary optical detection system for sample analysis, with the system including collection optics comprising a light concentrator, in accordance with aspects of the present disclosure.
Figure 2:
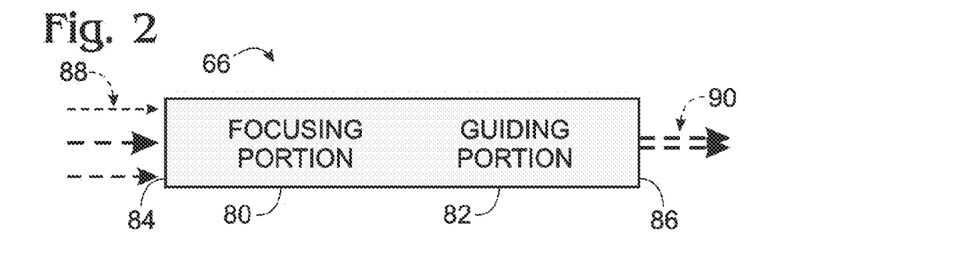
FIG. 2 is a schematic view of the light concentrator of FIG. 1.

This section provides an overview of exemplary optical detection systems for sample analysis, with the systems each including at least one light concentrator; see FIGS. 1 and 2.

FIG. 1 shows a schematic representation of an exemplary optical detection system 50 for sample analysis. Propagation of light through the system is represented by dashed linear arrows. Communication of signals and/or data is represented by a solid linear arrow.

Detection system 50 may include at least one light source 52 to generate illumination light 54 (interchangeably termed excitation light). Illumination optics 56 (interchangeably termed excitation optics) may control propagation of the excitation light to an examination region 58, where a sample 60 may be disposed.

The sample may photoluminesce in response to the excitation light, to generate emitted light 62. The emitted light may propagate through collection optics 64 (interchangeably termed emission optics) including at least one concentrator 66, to reach a detector 68. Signals 70 generated by detector 66 in response to detected light may be communicated to a data processor 72 that manipulates the signals to generate one or more values characterizing the sample, such as one or more values for an analyte level or activity in the sample.

Light source 52 may include any suitable mechanism for producing light. The light source may be a single light source or two or more light sources (e.g., with distinct spectral outputs). Each light source may be a constant source or a pulsed source, among others. Exemplary light sources include electroluminescent sources, such as light-emitting diodes (e.g., organic light-emitting diodes, polymer light-emitting diodes, solid-state diodes, etc.). Other exemplary light sources include lasers. Additional exemplary light sources include gas/high-intensity discharge lamps (e.g., mercury vapor lamps, xenon arc lamps, xenon flash lamps, neon and argon lamps, fluorescent lamps), incandescent lamps, and the like. In some cases, no separate light source may be necessary in the system if the sample is luminescent without photo-excitation (e.g., a sample that is chemiluminescent or bioluminescent, among others).

The excitation optics and/or collection optics each may include at least one optical element. The optical element may be configured to focus, direct, guide, simplify, mix, subtract, and/or disperse light, among others. Accordingly, the optical element may transmit, refract, reflect, diffract, diffuse, filter, homogenize (render more uniform, such as for intensity), and/or scatter light, among others. Exemplary optical elements may include mirrors, lenses, prisms, tubes, gratings, apertures, fibers, filters, combinations thereof, or the like. Filters, in turn, may include spectral filters (for changing the spectrum (color content) of light), neutral density filters (for changing the overall intensity of light), polarizing filters (for changing the polarization of light), spatial filters (for altering (e.g., cleaning up) the illumination profile), and/or diffusion filters (for homogenizing light), among others.

The examination region may include any suitable structure for holding a sample, optionally while the sample is being illuminated (excited) and/or is emitting light. Exemplary examination regions may include a support, a container for fluid, a stage, a platform, or any combination thereof, among others. The examination region may be optically coupled to the collection optics.

The sample may have any suitable characteristics. The sample may be a chemical and/or biological sample. The sample may contain any suitable analyte(s), such as one or more types of nucleic acid, protein, ion, lipid, carbohydrate, small molecule, cell, virus, etc. The sample may be aqueous and may be present as a bulk phase or a dispersed phase (e.g., droplets). Further aspects of samples, exemplary analytes, droplet formation, droplet manipulation and transport, and droplet detection are described in the patent documents listed above under Cross-References, which are incorporated herein by reference.

The detector may have any suitable characteristics. The detector may be a multi-pixel detector having a two-dimensional array of light-sensing elements (pixels) (e.g., more than 10 or 100 pixels). The array may be rectangular or may have any other suitable shape. In some cases, the light-sensing elements may be photomultipliers, such as silicon photomultipliers. Each photomultiplier may be an avalanche photodiode, and thus the detector may be composed of an array of avalanche photodiodes. In some cases, the detector may be a charge-coupled device (a CCD detector) or a complementary metal-oxide-semiconductor detector (a CMOS detector), among others. In any event, the detection area defined by the detector may have any suitable size, such as between about 0.0625 $mm^2$ (e.g., 0.25 mm×0.25 mm) and about 36 $mm^2$ (e.g., 6 mm×6 mm), among others. Each light-sensing element, in turn, may have any suitable size, such as transverse dimensions (e.g., widths) of between about 25 µm×25 µm and 100 µm×100 µm, among others.

The data processor may have any suitable characteristics. The processor may be described as a microprocessor and/or a controller, among others. The processor may be in wired or wireless communication with the detector or may require human intervention to communicate detected signals to the processor (e.g., manual transfer via a memory storage device).

FIG. 2 shows a schematic view of concentrator 66 of system 50. The concentrator may comprise a focusing portion 80 operatively connected to a guiding portion 82. The focusing and guiding portions may be fixed in relation to each other. The portions may be continuous with each other and provided together by a single piece. Accordingly, concentrator 66 may be described as a one-piece or unitary optical element.

The one-piece optical element may or may not be formed as a monolithic structure. In some cases, the one-piece optical element may be formed from two or more pieces that are permanently united in contact with one another to create a single piece. For example, the two or more pieces may be permanently united using an adhesive. The adhesive may have an optical index that is about the same as the optical index of each of the pieces, to minimize undesired optical effects at each interface created between a pair of the pieces. In some embodiments, the focusing portion and the guiding portion may be formed by discrete pieces that are united to produce a single-piece unit for use in the detection system.

Concentrator 66 may have, at opposing ends, a light entrance 84 (interchangeably termed an input aperture) and a light exit 86 (interchangeably termed an output aperture). Incident light 88, which may be collimated, can enter focusing portion 80 via light entrance 84. The focusing portion may refract incident light 88 to concentrate the light by decreasing the size of the light's beam (or light ray bundle) as the light propagates through the focusing portion (e.g., decreasing the diameter and/or cross-sectional area of the beam (or light ray bundle)). The guiding portion then may guide the concentrated light to light exit 86. The guiding portion may increase the transverse uniformity of the concentrated light, such that emerging light 90 is both more concentrated and more homogeneous in intensity than incident light 88.

Concentrator 66 is formed of optically transparent material. Suitable materials for the concentrator may include glass, fused silica, plastic (e.g., an optically clear plastic, such as polymethylmethacrylate (PMMA), polycarbonate, polystyrene, polyolefin, cyclic olefin copolymer, silicone, etc.), or the like. The concentrator can be constructed by machining (e.g., single-point diamond turned) and polishing, molding (e.g., injection-molded plastic), or a combination thereof, among others.

II. Detection System With Light Concentrators And Multi-pixel Detectors

This section describes exemplary optical detection systems having a pair of light concentrators each operatively connected to a respective multi-pixel detector; see FIGS. 3-15.

Figure 3:
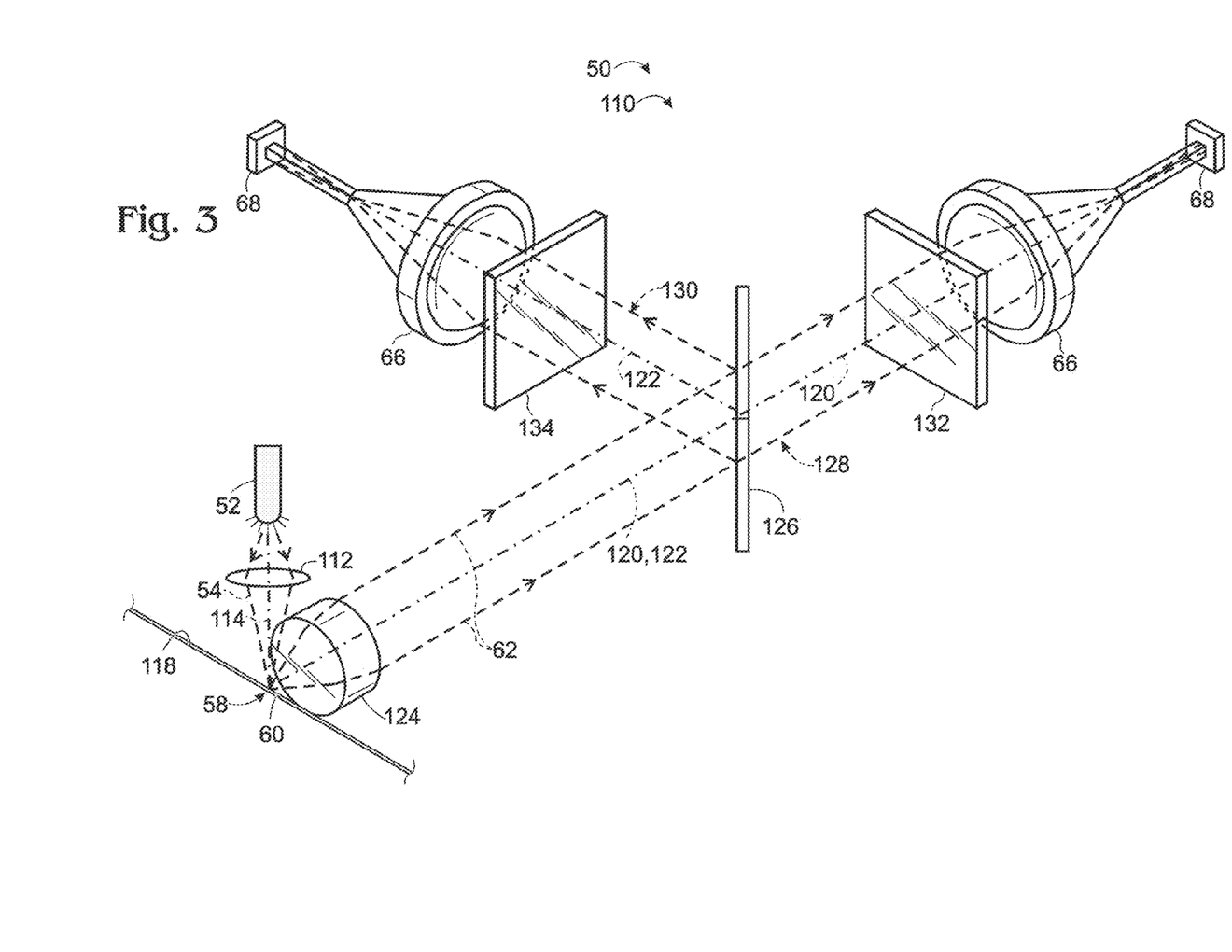
FIG. 3 is an isometric view of an exemplary embodiment of the optical detection system of FIG. 1 that includes two copies of an exemplary light concentrator, with illustrative light rays represented by dashed lines, in accordance with aspects of the present disclosure.
Figures 4, 5:
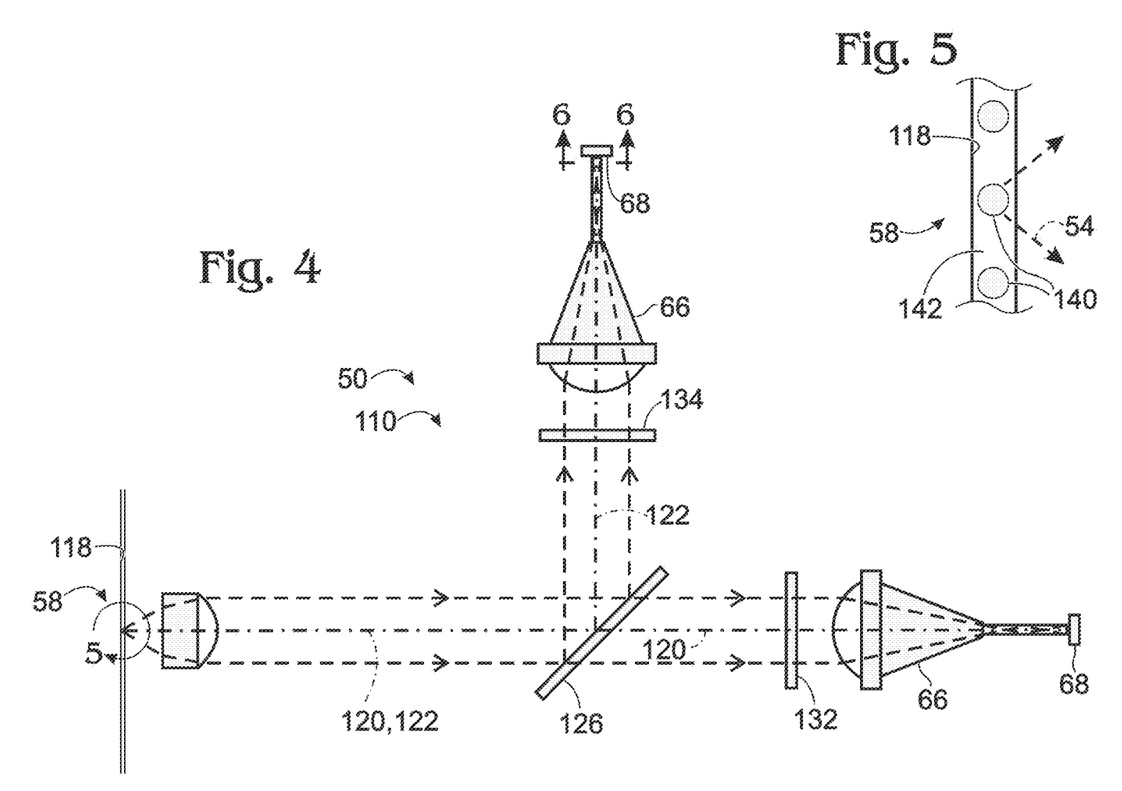
FIG. 4 is a plan view of the optical detection system of FIG. 3.
FIG. 5 is a fragmentary view of an examination region of the optical detection system of FIG. 4, taken generally at the region indicated at "5" in FIG. 4.

FIGS. 3 and 4 show respective isometric and plan views of an exemplary embodiment 110 of detection system 50 of FIG. 1. System 110 has two copies of light concentrator 66 and detector 68. FIG. 3 shows how the system is used for both illumination (excitation) and detection (emission); FIG. 4, in contrast, omits elements involved in illumination to emphasize the elements involved in detection.

Sample illumination may proceed as follows. Light source 52 may generate excitation light 54 that is directed to examination region 58 by excitation optics, such as at least one lens 112 and/or other optical element thereof, along an excitation axis 114. One or more filters operatively positioned between the light source and the examination region may be used to alter properties (e.g., spectrum, intensity, polarization, contrast, phase, etc.) of the excitation light. The examination region may be intersected by a channel 118 or other container that holds sample-containing fluid in, and/or carries the fluid through, the examination region.

Emitted light 62 may travel to distinct detectors 68 along optical axes 120, 122. The emitted light may be collimated by a collimation element 124, such as a planoconvex lens. The collimated light then may be split by a dichroic element 126. A first light portion 128 continues along optical axis 120 after passing through the dichroic element, and a second light portion 130 is reflected by dichroic element 126 for propagation along optical axis 122. Both light portions pass through respective spectral filters 132, 134 and a copy of concentrator 66, and each is finally incident on a detection area of one of detectors 68. One or more filters operatively positioned between the examination region and the detectors may be used to alter properties, such as those listed above, of the emitted light. For example, spectral filters 132, 134 may be selected to permit passage of distinct wavebands of light to the detectors. In some cases, neutral density (intensity) filters, operatively positioned before and/or after the spectral filters, may be used to adjust the intensity of light before it is incident on the detectors.

FIG. 5 shows a fragmentary, magnified view of examination region 58. Channel 118 may hold droplets 140 (e.g., aqueous droplets) disposed in a carrier phase 142, which may be immiscible with the droplets. The droplets may travel serially through examination region 58.

Figure 6:
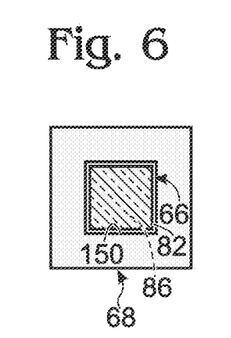
FIG. 6 is a sectional view of the detection system of FIG. 4, taken generally along line 6-6 of FIG. 4 through one of the light concentrators and toward a detector of the system.

FIG. 6 shows a region near an interface between one of concentrators 66 and one of detectors 68. Detector 68 may define a detection area 150, which may be formed by an array of photo-sensitive elements (e.g., avalanche photodiodes). Output aperture 86 of guiding portion 82 may correspond in size, shape, or both size and shape, to detection area 150. For example, here, both output aperture 86 and detection area 150 are rectangular. The widths of output aperture 86 and detection area 150 may differ from each other by less than about 40%, 20%, or 10%, among others. The areas of output aperture 86 and detection area 150 may differ from each other by less than about two-fold.

Figure 7:
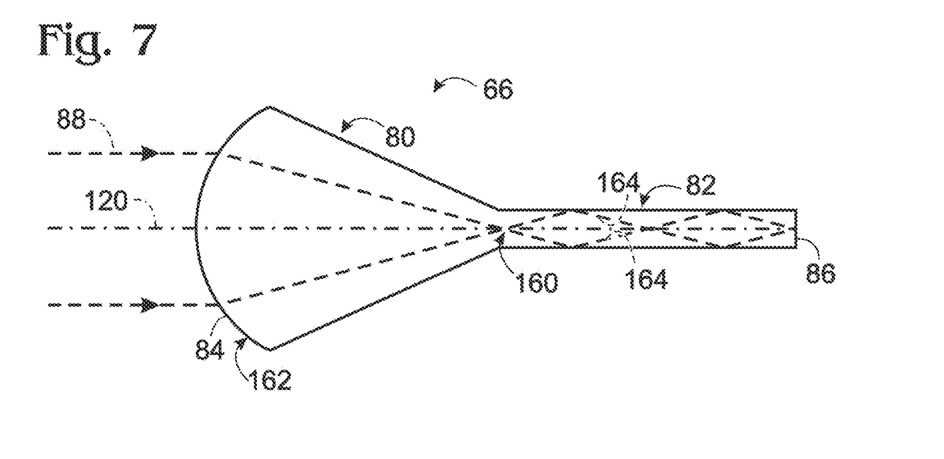
FIG. 7 is a somewhat schematic side view of a light concentrator of the optical detection system of FIG. 3.

FIG. 7 shows a somewhat schematic side view of concentrator 66. Incident collimated light 88 may be refracted by focusing portion 80 such that the rays of the incident light converge to a focal point 160. The focal point may be positioned at a junction of focusing portion 80 and guiding portion 82. In other words, focusing portion 80 concentrates the incident light to substantially reduce the cross sectional area of the light between input aperture 84 and the light entrance to guiding portion 82.

Input aperture 84 may be formed by a spherical or nearly spherical (aspherical (e.g., hyperbolic or ellipsoidal)) surface 162. The curvature of the input aperture may be selected according to the desired distance from the input aperture to focal point 160, with a larger radius of curvature of input aperture 84 moving the focal point farther from the input aperture, and a smaller radius of curvature moving the focal point closer to input aperture 84.

The focusing portion may have any suitable shape. Focusing portion 80 may or may not taper toward guiding portion 82. The taper may be linear, to produce a frustoconical region of the focusing portion, or may be nonlinear. The focusing portion may have a circular cross-sectional shape.

Guiding portion 82 may be structured to encourage propagation of the concentrated light along the guiding portion to output aperture 86. The guiding portion, which may be described as a waveguide or a waveguide portion, is configured to produce total internal reflection, indicated at 164, to minimize loss of light through the side walls of the guiding portion. In particular, the length of focusing portion 80, measured along optical axis 120, the diameter and curvature of input aperture 84, and/or the diameter of the ray bundle formed by incident light 88, may be selected such that the minimum ray angle of light entering guiding portion 82, measured orthogonal to the surface of guiding portion 82, is greater than the critical angle above which total internal reflection occurs. For example, if concentrator 66 is formed of a material having a refractive index of 1.5, the critical angle is about 42 degrees.

The guiding portion may have any suitable structure and characteristics. The guiding portion may be linear or may extend along a nonlinear path, which may be arcuate, angular, or a combination thereof, as needed or desired to allow output aperture 86 to approach (e.g., contact) and face the detection area of the detector. The guiding portion may have any suitable length relative to focusing portion 80, such as being shorter than, about the same length as, or longer than focusing portion 80. The guiding portion may have any suitable cross-sectional shape, such as polygonal (e.g., rectangular, such as a square), circular, elliptical, or the like. The cross-sectional shape may be constant or may be variable along the length of the guiding portion.

FIGS. 8-11 show various views of light concentrator 66. The concentrator may include a head 170 connected to a stem 172 (interchangeably termed a shaft). Head 170 may provide focusing portion 80, particularly input aperture 84 and a propagation region 174 that connects the input aperture to guiding portion 82. Propagation region 174 may be tapered, such as frustoconical, or may be cylindrical, among others. Head 170 also may be equipped with an annular flange 176. Flange 176 may offer a convenient structure for engagement with a bracket that mounts the concentrator to a support.

Figure 8:
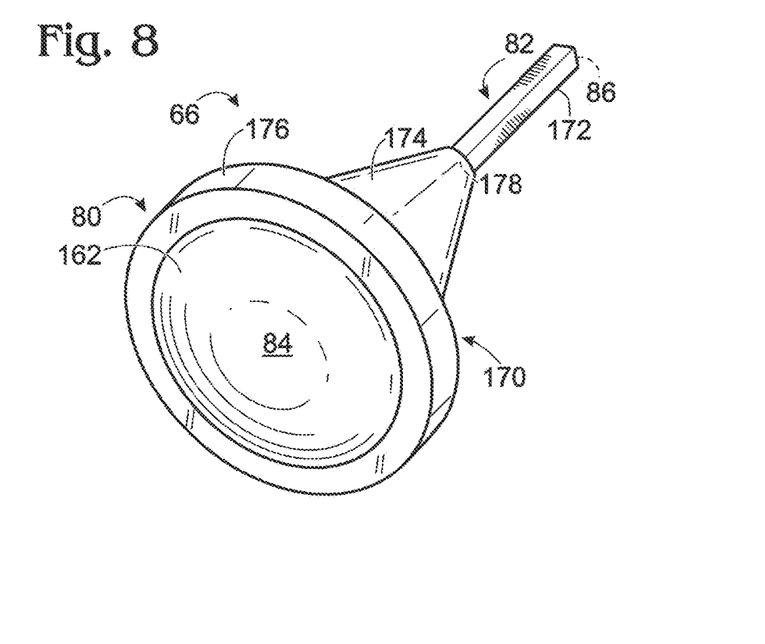
FIG. 8 is an isometric view of a light concentrator of the optical detection system of FIG. 3, taken generally from a light input end of the concentrator, in accordance with aspects of the present disclosure.
Figure 9:
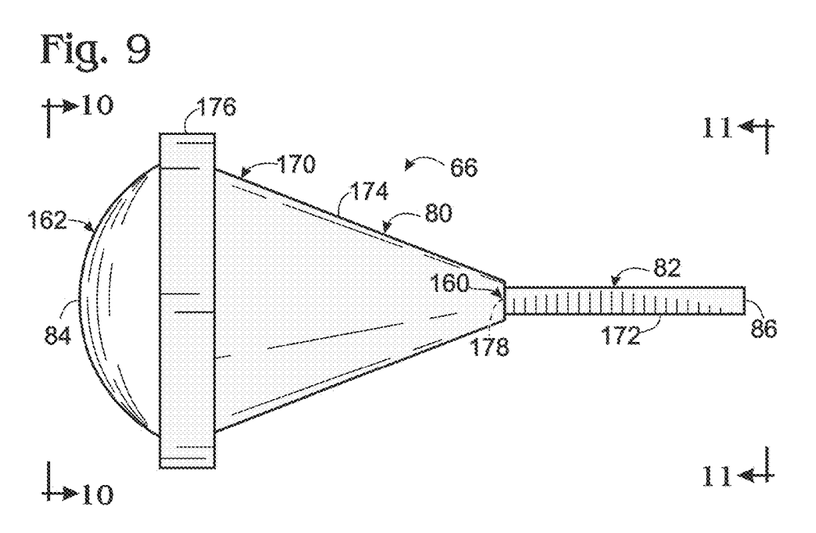
FIG. 9 is a side view of the light concentrator of FIG. 8.
Figures 10, 11:
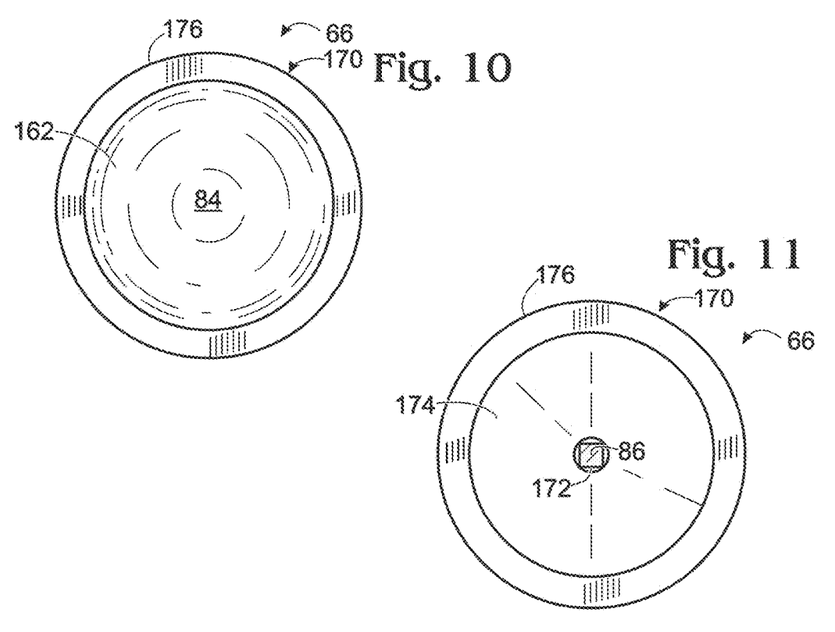
FIG. 10 is an end view of the light concentrator of FIG. 8, taken generally along line 10-10 of FIG. 9.
FIG. 11 is another end view of the light concentrator of FIG. 8, taken generally along line 11-11 of FIG. 9.

Stem 172 may have opposing ends that form a light entrance 178 to guiding portion 82 and output aperture 86 of concentrator 66. Entrance 178 may be positioned at focal point 160 of focusing portion 80 (see FIG. 9).

Concentrator 66 may be configured to concentrate incident light by any suitable amount. For example, the area of input aperture 84 may be at least about 10, 20, or 40 times greater than the area of output aperture 86.

Figure 12:
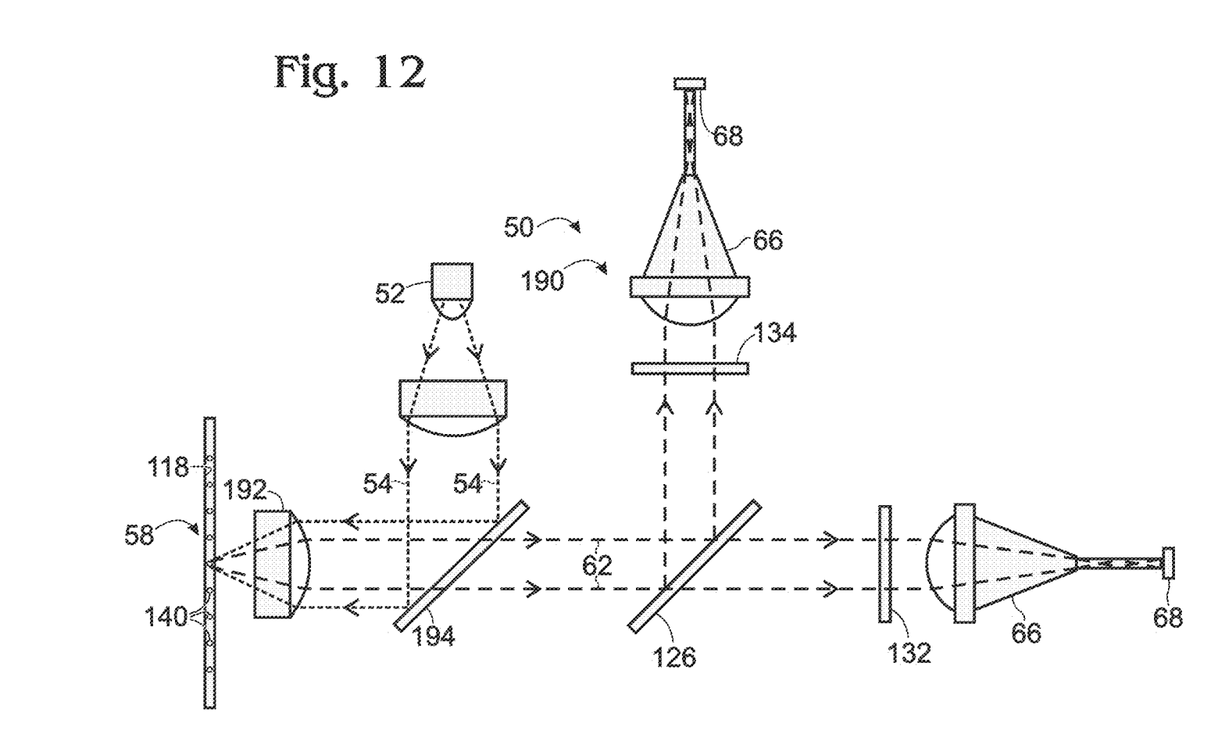
FIG. 12 is a plan view of an alternative exemplary embodiment of the optical detection system of FIG. 1, in which selected excitation and emission optics are combined, in accordance with aspects of the present disclosure.

FIG. 12 is a plan view of an alternative exemplary embodiment 190 of optical detection system 50 of FIG. 1. In this "epi-illumination" embodiment, the system uses common illumination and detection optics, and a common excitation and emission pathway, adjacent examination region 58. In contrast, in the "side-illumination" embodiment of FIGS. 3 and 4, the system used separate illumination and detection optics, and pathways, near the examination region. In other words, excitation optics element 112 and emission (e.g., collimation) optics element 124 in the embodiment of FIGS. 3 and 4 effectively have been replaced, in whole or in part, by a common optics element 192 that functions both to focus excitation light 54 from a light source 52 onto a sample in examination region 58 and to collect emission light 62 emitted by the sample and to direct it toward detectors 68. Excitation and emission light may be directed and separated using any suitable mechanism, such as a suitably positioned dichroic mirror 194. Other components of this embodiment may be substantially or wholly as described above.

III. Selected Embodiments

This example describes selected embodiments of the present disclosure related to optical detection systems including a light concentrator, and methods of using the detection systems for sample detection. The selected embodiments are presented as a series of numbered paragraphs.

1. A detection system, comprising: (A) an examination region; (B) a one-piece optical element including a focusing portion to concentrate light received from the examination region and a guiding portion to homogenize concentrated light received from the focusing portion; and (C) a detector configured to detect homogenized light received from the guiding portion.

2. The system of paragraph 1, wherein the guiding portion has a light entrance and a light exit, and wherein the focusing portion creates a focal point at the light entrance of the guiding portion.

3. The system of paragraph 1 or paragraph 2, further comprising a channel configured to carry fluid through the examination region.

4. The system of paragraph 3, wherein the channel contains droplets disposed in a carrier phase.

5. The system of any of paragraphs 1 to 4, wherein the focusing portion includes a surface through which light is received from the examination region, and wherein the surface is spherical or aspherical.

6. The system of paragraph 5, wherein the surface is aspherical.

7. The system of paragraph 5 or 6, wherein the optical element defines a long axis, and wherein the surface is centered on the long axis.

8. The system of any of paragraphs 1 to 7, wherein the optical element defines a long axis, and wherein the focusing portion includes a conical region centered on the long axis.

9. The system of any of paragraphs 1 to 8, wherein the guiding portion has a rectangular cross section.

10. The system of any of paragraphs 1 to 9, wherein the guiding portion is configured to permit propagation of light through the guiding portion by total internal reflection.

11. The system of any of paragraphs 1 to 10, wherein the detector is a multi-pixel detector.

12. The system of paragraph 11, wherein the detector includes an array of avalanche photodiodes.

13. The system of paragraph 11 or paragraph 12, wherein the detector has a plurality of light-sensing elements defining a detection region, and wherein the detector is positioned such that a majority of the detection region receives light that has traveled through the optical element.

14. The system of any of paragraphs 1 to 13, further comprising a light source that illuminates the examination region.

15. The system of paragraph 14, wherein the light source includes a light-emitting diode.

16. The system of any of paragraphs 1 to 15, wherein the optical element has an input aperture and an output aperture, and wherein the input aperture is at least about ten-fold larger in area than the output aperture.

17. A detection system, comprising: (A) an examination region; (B) a one-piece optical element including a head to concentrate light received from the examination region and a stem to homogenize concentrated light received from the head; and (C) a multi-pixel detector configured to detect homogenized light received from the stem.

18. A method of sample examination, comprising: (A) disposing at least a portion of a sample in an examination region; (B) concentrating light from the examination region with a one-piece optical element; (C) homogenizing the concentrated light with the optical element; and (D) detecting homogenized light received from the optical element.

19. The method of paragraph 18, wherein the at least a portion of a sample is disposed in droplets, and wherein the droplets are disposed in a carrier phase.

20. The method of paragraph 18 or paragraph 19, wherein the step of disposing at least a portion of a sample includes a step of driving fluid through the examination region.

21. The method of any of paragraphs 18 to 20, wherein the step of concentrating light is performed by focusing collimated light rays.

22. The method of paragraph 21, further comprising a step of collimating light rays from the examination region before such light rays are received by the optical element.

23. The method of any of paragraphs 18 to 22, wherein the step of detecting homogenized light includes a step of detecting light with a multi-pixel detector.

24. The method of any of paragraphs 18 to 23, further comprising a step of illuminating the examination region to produce emitted light, and wherein at least a portion of the emitted light is concentrated by the optical element.

25. The method of any of paragraphs 18 to 24, further comprising a step of determining a property of an analyte of the sample based on the light detected.

26. The method of paragraph 25, wherein the analyte is a nucleic acid.

27. The method of paragraph 25 or paragraph 26, wherein the property is a concentration of the analyte.

28. The method of paragraph 27, wherein the concentration is a concentration of the analyte in droplets.

29. The method of any of paragraphs 18 to 28, wherein the homogenized light detected includes light produced by photoluminescence in the examination region.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of sample examination, the method comprising:
disposing at least a portion of a sample in an examination region, wherein the at least a portion of a sample is disposed in droplets, and wherein the droplets are disposed in a carrier phase;
illuminating the examination region such that the sample emits light;
concentrating emitted light from the examination region with a one-piece optical element;
homogenizing the intensity of the concentrated light with the optical element by internal reflection; and detecting light of homogenized intensity received from the optical element.

2. The method of claim 1, wherein the step of concentrating emitted light is performed by focusing collimated light rays.

3. The method of claim 1, wherein the step of detecting light of homogenized intensity includes a step of detecting light with a multi-pixel detector.

4. The method of claim 1, wherein the step of concentrating emitted light is performed with a focusing portion of the optical element, wherein the step of homogenizing the intensity of the concentrated light is performed with a guiding portion of the optical element, wherein the guiding portion has an entrance end at which concentrated light passes from the focusing portion to the guiding portion, and wherein the step of concentrating emitted light includes a step of focusing emitted light on the entrance end of the guiding portion.

5. The method of claim 1, further comprising a step of receiving emitted light from the examination region through a substantially spherical surface of the optical element.

6. The method of claim 1, wherein the optical element has a rectangular end at which light of homogenized intensity exits the optical element, and wherein the step of detecting light of homogenized intensity is performed with a detector defining a detection area corresponding in size and shape to the rectangular end of the optical element.

7. The method of claim 1, wherein the step of homogenizing the intensity of the concentrated light includes a step of passing concentrated light through an elongated guiding portion having a rectangular cross section.

8. The method of claim 1, wherein the sample contains a fluorophore from which the light is emitted.

9. The method of claim 1, wherein the droplets are aqueous droplets.

10. The method of claim 1, wherein the carrier phase includes oil.

\* \* \* \* \*